US008096948B2

(12) United States Patent
Schreckenberg et al.

(10) Patent No.: US 8,096,948 B2
(45) Date of Patent: Jan. 17, 2012

(54) METHOD AND APPARATUS FOR DETECTING MOVEMENTS OF AN OBJECT USING VOLUME CHANGE

(75) Inventors: Marcus Schreckenberg, Freising (DE); Alexander Rossmanith, Germering (DE); Rolf Baumann, Munich (DE); Stam Kapetanakis, London (GB); Mark Monaghan, Croydon Surrey (GB)

(73) Assignee: Tomtec Imaging Systems GmbH (DE)

( * ) Notice: Subject to any disclaimer, the term of this patent is extended or adjusted under 35 U.S.C. 154(b) by 969 days.

(21) Appl. No.: 10/558,602

(22) PCT Filed: Nov. 25, 2004

(86) PCT No.: PCT/EP2004/013387
§ 371 (c)(1),
(2), (4) Date: Feb. 20, 2008

(87) PCT Pub. No.: WO2006/056221
PCT Pub. Date: Jun. 1, 2006

(65) Prior Publication Data
US 2008/0132788 A1 Jun. 5, 2008

(51) Int. Cl.
*A61B 8/00* (2006.01)
(52) U.S. Cl. ........ 600/443; 600/437; 600/438; 600/440; 600/450; 600/413; 600/428
(58) Field of Classification Search ................... 600/437, 600/438, 440, 443, 450, 413, 428
See application file for complete search history.

(56) References Cited

U.S. PATENT DOCUMENTS

| | | | | |
|---|---|---|---|---|
| 5,568,811 | A | | 10/1996 | Olstad |
| 5,669,387 | A | * | 9/1997 | Mine ............................. 600/455 |
| 6,135,959 | A | * | 10/2000 | Murashita et al. ............ 600/443 |
| 2005/0113670 | A1 | * | 5/2005 | Salla et al. .................... 600/413 |

FOREIGN PATENT DOCUMENTS

| | | |
|---|---|---|
| EP | 0 961 135 | 12/1999 |
| EP | 1 430 837 | 6/2004 |

OTHER PUBLICATIONS

International Search Report; PCT/EP2004/013387; Jul. 25, 2005.
"Written Opinion of the International Searching Authority regarding PCT/EP2004/013387"; Jul. 25, 2005.

* cited by examiner

*Primary Examiner* — Brian Casler
*Assistant Examiner* — Rajeev Siripurapu
(74) *Attorney, Agent, or Firm* — Cantor Colburn LLP

(57) ABSTRACT

The present invention relates to a method and apparatus for visualizing movements of an object, preferably the movements of blood vessels during the cardiac cycle. The method includes scanning the object by at least a two dimensional ultrasonic image scanning apparatus at discrete acquisition times to acquire a data set by using surface reconstruction and/or volume rendering techniques. Next, the three-dimensional data set is partitioned into a plurality of volume units, wherein each volume unit has a unit surface. The method further includes calculating the change of volume of each volume unit over the acquisition times to obtain level information of each corresponding unit surface over time, and displaying the three-dimensional data set with its level information over time.

17 Claims, 4 Drawing Sheets

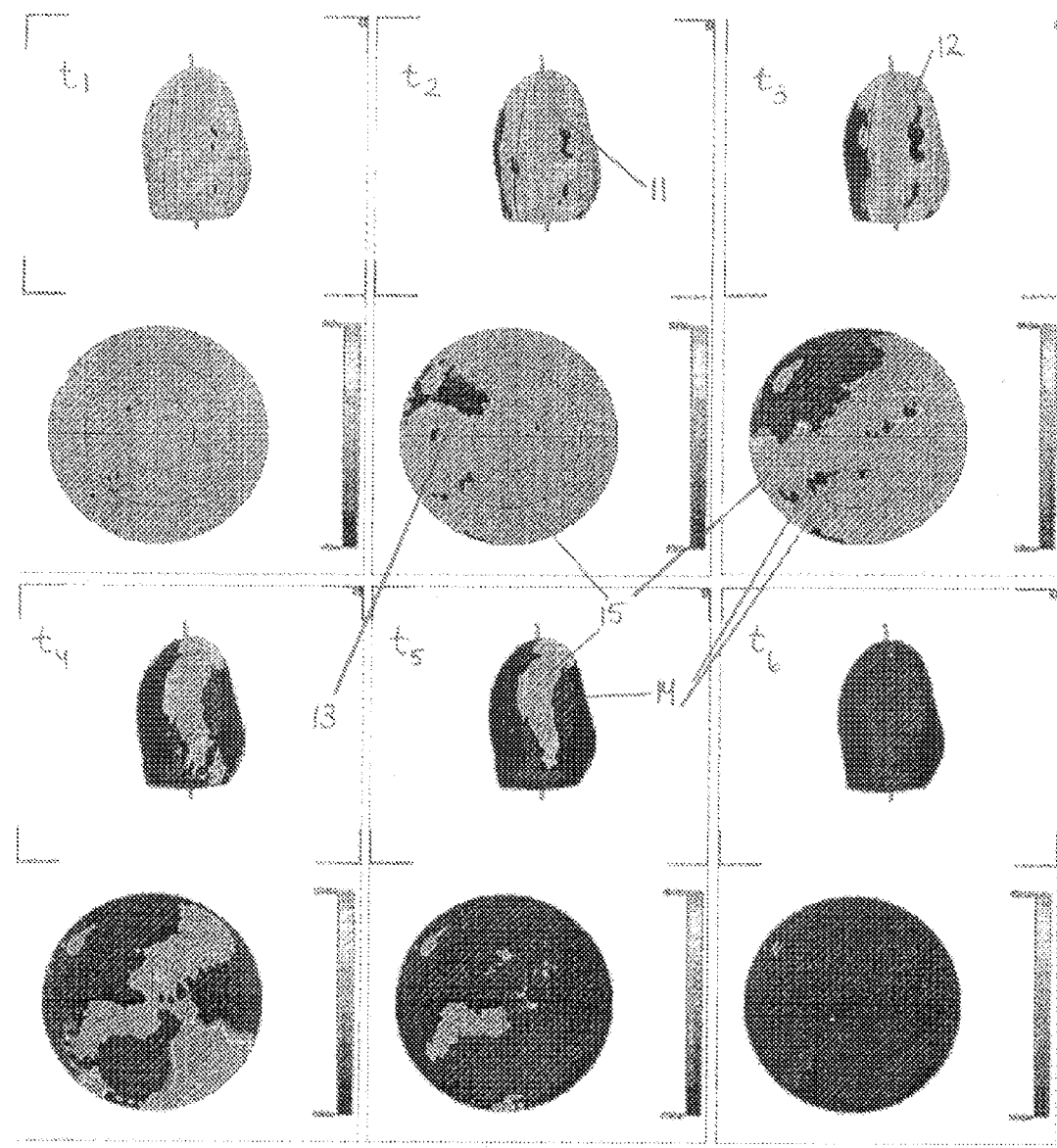

METHOD AND APPARATUS FOR DETECTING MOVEMENTS OF AN OBJECT USING VOLUME CHANGE

FIELD OF THE INVENTION

The present invention relates to a method and apparatus for detecting movements of objects, preferably the movements of muscle tissue during the cardiac cycle, more preferably to an ultrasonic method and apparatus for detecting the movements of parts of muscle tissue, such as the contraction pattern of ventricles and atria, in accordance with the preamble of independent claim 1 and independent claim 11. More specifically, the invention relates to a method and an apparatus for visualizing the contraction pattern of the heart of a human or animal body and to present a graphical representation of the surface of e.g. a heart chamber in order to detect whether it has a synchronous or asynchronous contraction.

BRIEF DISCUSSION OF THE RELATED ART

Presently, methods and apparatus are known for ultrasonic three-dimensional imaging wherein an object is scanned by two- or three-dimensional ultrasonic image scanning means in order to acquire cross-sectional images of the object wherein the discrete acquisition time of each cross-sectional image is recorded together with the image information. Thereafter, each of said cross-sectional images is digitalized and recorded together with its corresponding position and acquisition time. It is also well-known in the art to transform said cross-sectional images into a two- or three-dimensional data set by using surface reconstruction and/or volume rendering techniques and to display the three-dimensional data set over time, thereby showing a graphical representation of the scanned object in a three-dimensional manner which can be animated by displaying the three-dimensional representation at these discrete acquisition times. It is also well known in the art to acquire volume data with its corresponding resolution in space and time.

EP 0961 135 A1 discloses a method and an apparatus for rapidly generating a wire-frame volume model of the scanned object and how to display the surface of the object by interpolating over the wire-frame volume model. Thereby, it is possible to visualize e.g. the heart of a patient three-dimensionally as well as its movement over time in a virtual reality surface shell.

Nevertheless, ultrasonic scanning of the heart (echocardiography) has presented special challenges and problems because of the relatively complex movement of the heart and dynamic changes in the heart's configuration that occur during the cardiac cycle. Because of these problems and others, cardiac ultrasonic scanning historically has been limited to two- or three dimensional imaging wherein it has not been possible in an acceptable manner to view or visualize myocardial contraction throughout the cardiac cycle. For cardiologists and electro physiologists it is extremely important to understand the contraction pattern of heart muscle, in particular ventricles and atria. A regular synchronous contraction leads to optimal results in cardiac function. Inter- or intraventricular conduction disturbances can lead to asynchronous contraction of the heart chambers and thus reduce the function and efficiency of the heart. The current methods to assess asynchronous contraction are limited and labor intensive. Up to now the propagation of the contraction of the inner surface of heart chambers was examined throughout other imaging modalities like CT or MRI (Magnetic Resonance Imaging). Nevertheless, these techniques are not widespread as both acquisition and analysis of the movement of the chamber walls of the heart are time-consuming and complex.

Currently, MRI and CT techniques are able to provide static parameter distribution, thereby visualizing the contraction pattern of the ventricles two-dimensionally by using color coding (functional imaging). A drawback is the limited number of colors that can be differentiated by a human eye. Furthermore, the interpretation of color maps is usually non-intuitive with respect to local differences. For example, there is no natural interpretation for "yellow" being larger or smaller than "green". A workaround is the usage of a color map with a limited number of colors (e.g. blue and red) and smooth transitions. However, although the interpretation gets more intuitive, the differentiation between neighboring color levels becomes more difficult. Thus, usually only a limited interval of values is mapped at a time without a global overview of the propagation of the contraction of the heart surface.

BRIEF SUMMARY OF THE INVENTION

The invention provides an ultrasonic method and apparatus for detecting movements of objects in a quick and reliable manner, and especially provides a method and apparatus which allows quick and reproducible assessment of the contraction of a blood vessel, such as a heart muscle, especially to visualize the propagation of the contraction wave over the surface of a human's heart over time, especially the inner surface of heart chambers.

At the same time the invention provides a method and an apparatus which obtains the above described information non-invasive and quick to reduce examination time thereby being as accurate as possible.

The claimed ultrasonic method for detecting movements of objects comprises the steps of scanning an object by image scanning means, preferably two- or three-dimensional ultrasonic image scanning means, acquiring at least two-dimensional cross-sectional images of that object at discrete acquisition times, digitalizing each of that cross-sectional images, recording each of these cross-sectional images and its corresponding position and acquisition time, transforming these cross-sectional images into a three-dimensional data set by using surface reconstruction and/or volume rendering techniques and displaying said three-dimensional data set over time wherein the three-dimensional data set is partitioned into a plurality of volume units, each volume unit has a unit surface and wherein the change of the volume of each volume unit is calculated over said acquisition times in order to obtain level information of each corresponding unit surface over time and wherein said level information is then displayed. This procedure also applies to acquisition methods where three-dimensional datasets are generated directly.

Preferably, two-dimensional ultrasonic image scanning means are used to acquire two-dimensional cross-sectional images of that object. However, it is also possible to use a three-dimensional ultrasonic image scanning means to acquire three-dimensional cross-sectional images which are volumes of said object. The term "cross-sectional image" therefore encompasses both possibilities.

While the invention uses known techniques to obtain a three-dimensional data set in order to display the contours of the object under examination, e.g. the heart during a cardiac cycle, it is now surprisingly possible with using an ultrasound apparatus to display the movement of the inner surface of the heart chambers during the cardiac cycle. In order to obtain singular information on the synchronicity of the contraction of the heart for each sub-set or segment of the heart surface, the present invention partitions said three-dimensional data set into a plurality of volume units and calculates the change of volume in order to obtain level information of a discrete and small surface unit of the object. Throughout such method it is possible to visualize the contraction front of a human's heart chambers in a three- or four-dimensional way.

Preferably, the level information of each of the unit surfaces is a range of colors or a range of grey values in order to easily visualize at which "level or location" the surface of each volume unit is. The three-dimensional data set is preferably partitioned into a plurality of volume units by using a center of gravity within the object under examination and by linking all corners of said unit surface with the center of gravity. Thereby, the whole object is partitioned into said plurality of volume units, each being a three-dimensional segment of the object under examination.

At the same time it is advantageous to also partition the level information thereby using discrete level borders and allocating a limited number of colors, preferably two or three, to said discrete level information. Thereby, it is possible to visualize two or three positions of the surface of each volume unit in a simple manner, thereby indicating whether the surface is in a "contracted" state or an "expanded" state. By displaying the level information three-dimensionally or two-dimensionally over time it is possible to visualize the movement of the surface of the object like the propagation of a contraction wave over the surface of a heart during the cardiac cycle.

Even more preferably, the unit surfaces alone with their corresponding level information are displayed two-dimensionally on a two-dimensional map by using two-dimensional transformation methods which are per se known.

By visualizing the three-dimensional object two-dimensionally (like the two-dimensional world map of the earth) it is possible to visualize the movement of each segment of the surface of the object throughout a color representation of the two-dimensional surface of segment. Since the borders between the colors will move across the two-dimensional image it is possible to follow the e.g. propagation wave of the contraction of a heart chamber.

In accordance with a preferred embodiment of the present invention the propagation of said level information is displayed over time on said two-dimensional map wherein additionally two-dimensional propagation vectors may also be displayed. By using the length and direction of said two-dimensional propagation vectors it is possible to visualize the direction, amount and speed of volume change of respective volume units as well as their respective main positions and their numbers on said map. If a plurality of neighbouring volume units move at the same time into the same direction but earlier or later then volume units at other places of the object, the propagation vector will have a direction from the first group of volume units to the second group of volume units wherein the length of the propagation vector is a measure for the speed of the wave propagation and/or the difference in volume change. Here, the change of volume of each volume unit is preferably calculated by the application of noise reduction algorithms, edge enhancement algorithms and/or spatial artifacts reduction algorithms.

The discrete acquisition times for a cardiac object are preferably selected in accordance with an algorithm considering hearth cycle variations by electrocardiographic gating and/or respiratory cycle variations by impedance measurements. Theses are generally known in the state of the art.

The apparatus in accordance with the present invention comprises two- or three dimensional ultrasonic scanning means for scanning an object in order to acquire cross-sectional images of said object at discrete acquisition times as well as digitalizing means for digitalizing each of said cross-sectional images, recording means for recording each of said cross-sectional images and its corresponding position and acquisition time, transforming means for transforming said cross-sectional images into a three-dimensional data set by using surface reconstruction and/or volume rendering techniques and displaying means for displaying said three-dimensional data set over time as well as partitioning means which partition the three-dimensional data set into a plurality of volume units, each volume unit having a unit surface, calculating means which calculate the change of volume of each volume unit over said acquisition times in order to obtain level information of each corresponding unit surface overtime wherein displaying means display said level information.

The calculating means are preferably able to define a center of gravity which is one corner of all volume units which other corners are all included in the surface of the object. Thereby, it is guaranteed that a change in volume of each volume unit results in a level change of the respective unit surface. Said partitioning means partition said level information preferably by using discrete level borders and by allocating a limited number of colors, preferably two or three, to said discrete level information. At the same time transformation means transform said unit surfaces with their respective level information into a two-dimensional map over time by using known two-dimensional transformation methods and said displaying means preferably display the level information two-dimensionally.

The apparatus furthermore comprises electrocardiographic gating means and respiration trigger means for dynamically scanning cardiac objects. At the same time said apparatus has displaying means which are capable of displaying the two-dimensional map of the present invention and a two-dimensional map of an electrophysiological mapping system thereby being able to compare the propagation of the potential level and the propagation of the contraction level of each segment of the surface of a heart in order to provide reliable information for heart diagnosis for a doctor.

BRIEF DESCRIPTION OF THE DRAWINGS

Some preferred embodiments of the present invention will be explained in conjunction with the drawings as follows:

FIG. 3a shows one segment of FIG. 3 partitioned in a plurality of volume units, FIG. 3b shows one volume unit of FIG. 3a, FIG. 4 shows the change of volume of the volume unit of FIG. 3b over time, FIG. 7 shows 6 three-dimensional and two-dimensional representations of the object of FIG. 3 at 6 different acquisition times.

DETAILED DESCRIPTION OF THE INVENTION

Figure 1A:
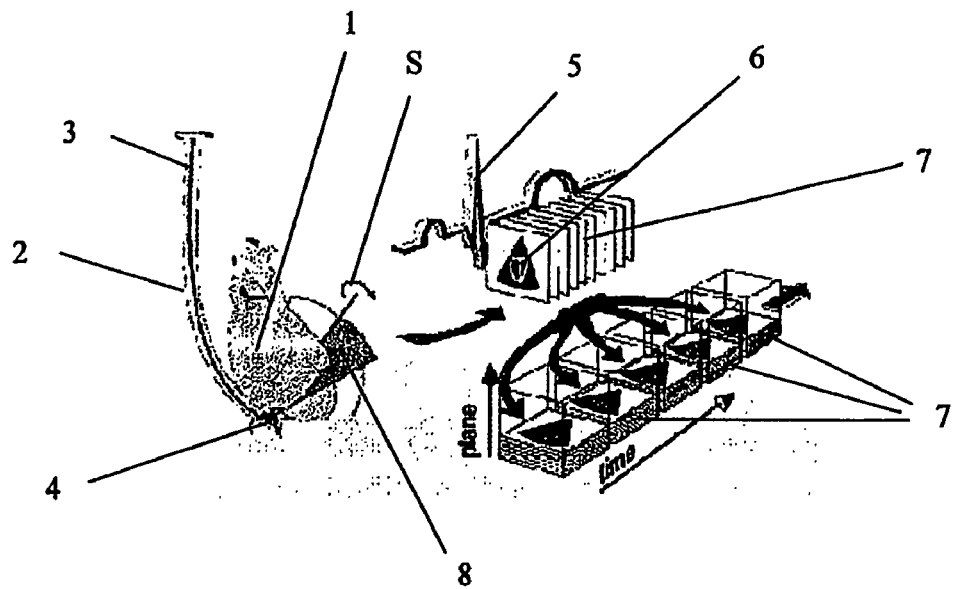
FIG. 1a shows an endoscope echocardiographical acquisition.

FIG. 1a shows an object 1 like an internal organ or tissue (e.g. heart) which is scanned by an ultrasonic beam 8 from scanning means 4 like a transducer which is incorporated within a probe situated in a vene or arteries adjacent to the object 1 (such as in the esophagus adjacent to the heart chamber) wherein the scanning means 4 are linked with processing means (not shown) by an endoscope connection 3 within the endoscopical path 2. The transesophageal probe 4 houses a rotational-array transducer at a distal end of a standard endoscope. The scanning plane can be continuously rotated through 180° starting from a longitudinal imaging position via a control knob on the handle of the echoscope. The cardiac cross-sections encompass a cone shaped volume with its point originating in the transducer (compare also FIG. 1b). Then a step motor is activated by the steering logic which controls the image acquisition in a given plane by an algorithm considering heart cycle variation by ECG-gating 5 and respiratory cycles variation by impedance measurement. For each position of the heart (e.g. systole or diastole) the heart is scanned by acquiring a series of cross-sections 6, thereby obtaining a set of cross-sectional images 7 which belong to a certain position of the heart (which is similar to a stroboscopical picture representing a certain position of the heart at each acquisition time t1, t2, . . . t6).

Figure 1B:
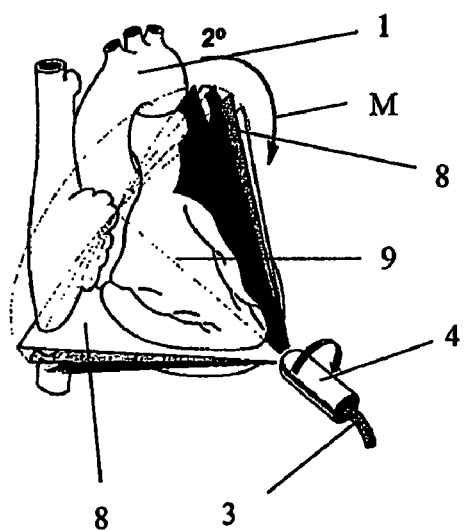
FIG. 1b shows the principle of acquisition of sequentional cross-sectional images of a heart.

FIG. 1b shows an enlarged view of the principle of acquisition of sequential cross-sections 6. A transducer 4 being linked to the computer by an endoscope connection 3 scans the heart 1 consisting of the left ventricle 11 and right ventricle 10 by acquiring all acquisition planes 9 throughout the ultrasonic beam 8, thereby sweeping the ultrasonic beam in a direction S.

Figure 2:
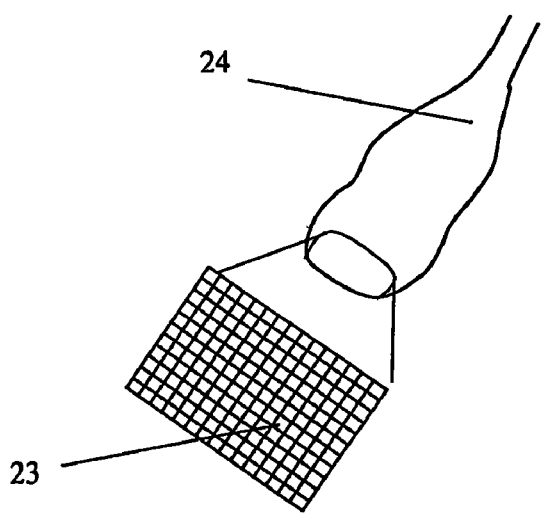
FIG. 2 shows an example of a three-dimensional transducer probe.

FIG. 2 shows an example of a three-dimensional ultrasonic image scanning means, such as a transthoracic probe 24 which is able to acquire a matrix 23 of 3-D image elements. Herewith, three-dimensional cross-sectional images, namely volumes, can be acquired. Other image acquisition techniques are also possible, such as an ultrasonic catheter-probe.

Figure 3:
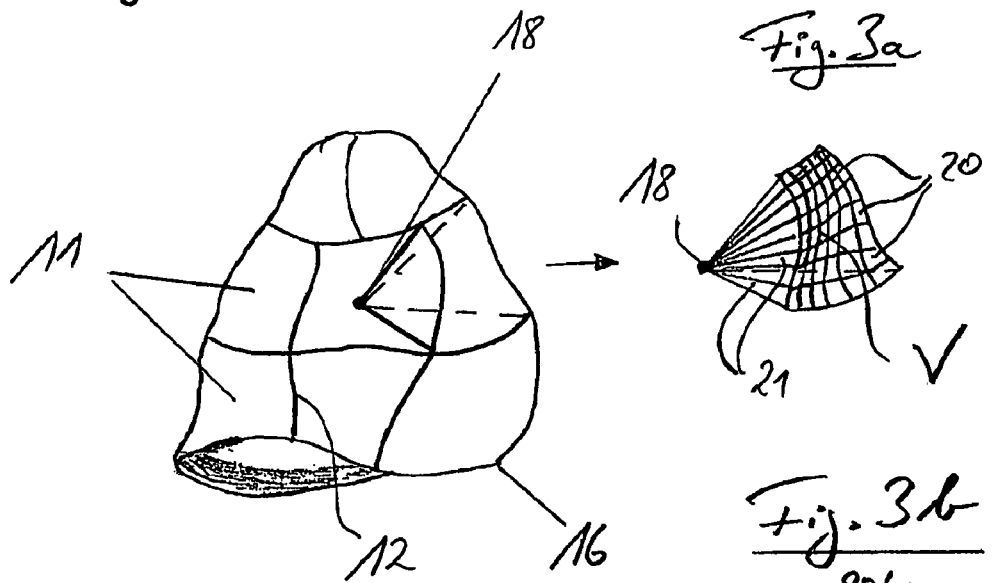
FIG. 3 shows schematically the segmented surface of a three-dimensional object.

FIG. 3 shows schematically the three-dimensional representation of the surface of the object 1 which is divided into segments 11 having segment borders 12. The three-dimensional volume 16 can be further divided into a plurality of volume units 21 each having a unit surface 20. Such partitioning is preferably done by linking each corner (in FIG. 3a each volume unit has four corners on the surface) on the surface with a center of gravity 18 which is located inside the three-dimensional volume 16. As shown in FIG. 3b, each volume unit 21 has a unit surface 20 which expands or contracts through various levels since the center of gravity 18 is at a fixed position. Whenever the volume of the three-dimensional volume 16 changes the volume change $\Delta V$ of each volume unit 21 results in a level change of the unit surface 20.

As shown in FIG. 3b three levels 13, 14 and 15 are divided by level borders 10 which are predeterminable. Whenever the time change $\Delta T$ is sufficient to raise the unit surface over a level border 10 the surface will receive—in accordance with a preferred embodiment of the present invention—another discrete level information such as another color. It is therefore possible to allocate e.g. the color blue to the first level 13, the color grey to the second level 15 and the color red to the third level 14.

Whenever the unit surface 20 is within one of the three above mentioned levels 13, 14 or 15 the surface will be allocated a certain level information e.g. the color blue for being in the first level 13. The respective unit surface 20 of the volume unit 21 as shown in FIG. 3a will then be colored blue.

Figure 4:
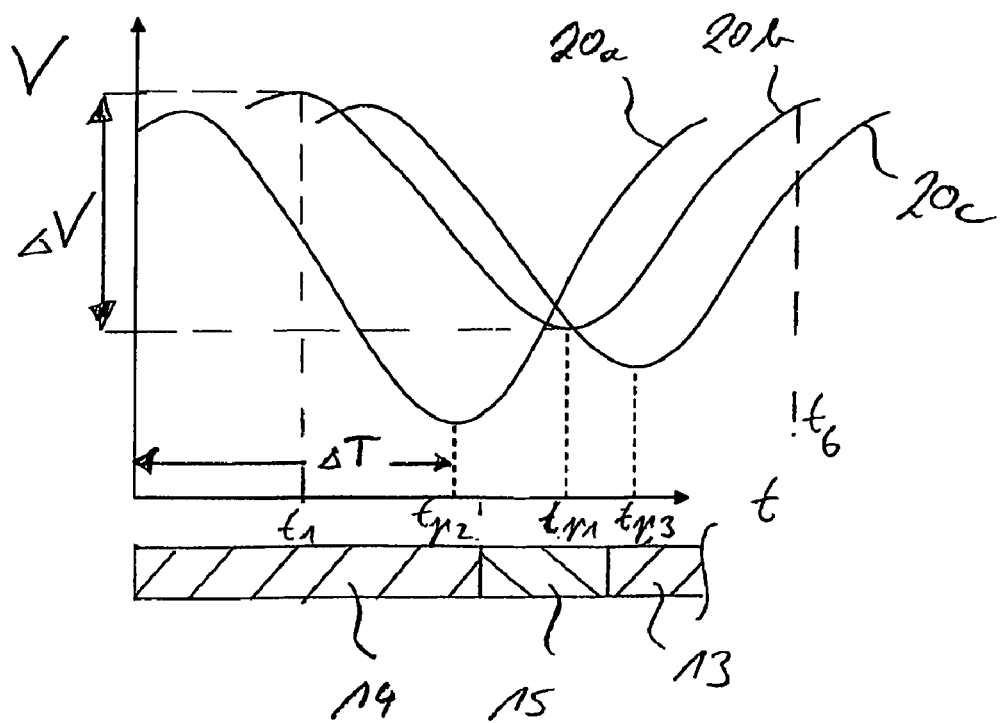

FIG. 4 shows the volume change $\Delta V$ of three volume units 20a, 20b and 20c (20b of FIG. 3b) over time. If the cardiac cycle of a heart is examined t1 is the time shortly after the end of the diastole, $t_p$ is the time at the end of the systole and t6 is the time shortly before the enddiastole. At the time $t_p$ the volume unit 20b has reached its lowest volume so that the unit surface 20b has reached its lowest level. The respective time $t_p$ is not the time when all volume units 20a, 20b or 20c reach their smallest volume but only the time at which one singular volume unit 20b reaches its lowest volume. Other volume units 21 reach their lowest "position" at other times of lowest volume $t_{p2}$, $t_{p3}$ between t1 and t6.

As can be seen from FIG. 4, all volume units 20a, 20b and 20c received different level information, namely the first volume units 20a the information 14, since the time of the lowest volume $t_{p2}$ is in the area 14, the second volume units 20b (of FIG. 3b) the information 15, since the time of the lowest volume $t_{p1}$ is in the area 15 and the third volume units 20c the information 13, since the time of the lowest volume $t_{p3}$ is in the area 14. When "moving" the level information along time, each volume unit will receive different level information, such as colors, over time and hence, it is possible to visualize the contraction wave as a movie. Statically, each volume unit has a certain "time stamp" $\Delta T$, namely the time necessary to reach the time of lowest volume $t_p$.

Figure 5:
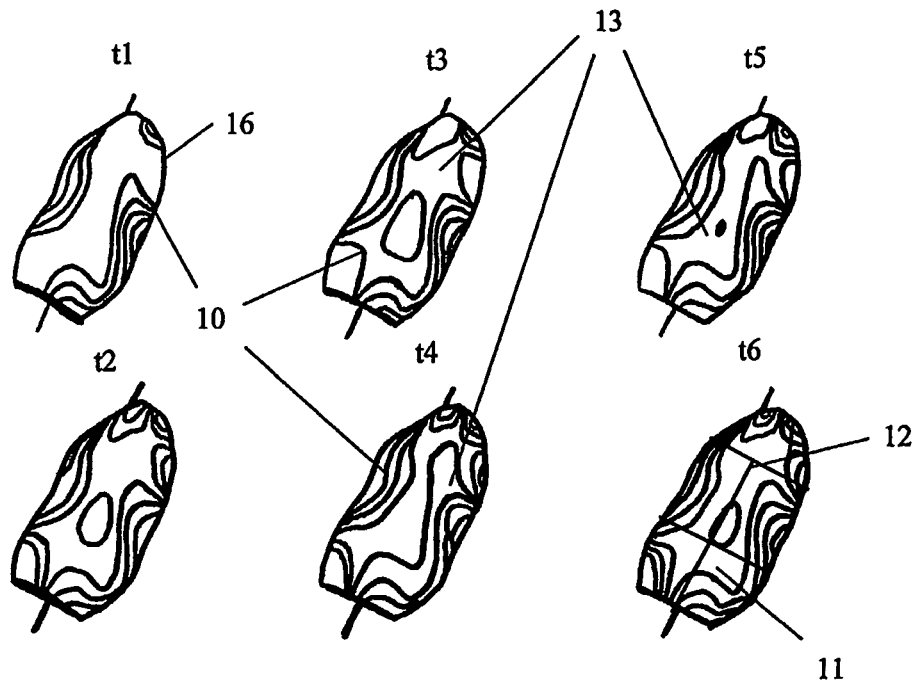
FIG. 5 shows one partial segment of the object of FIG. 3 with lines of equal contraction levels at 6 different times.

FIG. 5 shows a dynamic display of a two-dimensional surface in a three-dimensional space. The volume 16 is partially shown in FIG. 5 with the level borders 10 displaying the borders of various levels 13, 14 and 15. The first level 13 indicates wall segments that have already reached their peak contraction. From t1 to t2 the color limits are shifted so that the color for level 13 is addressed to level 14 and for t3 addressed to level 15 and so on. This way a certain color indicates the regions that are momentarily in their peak contraction phase and following the propagation of the color over time displays the mechanical muscle contraction front of the heart chamber. The contraction front of the heart chamber propagates over time since the various segments 20 of the inner surface of the heart chamber move at different times into different directions.

Figure 6:
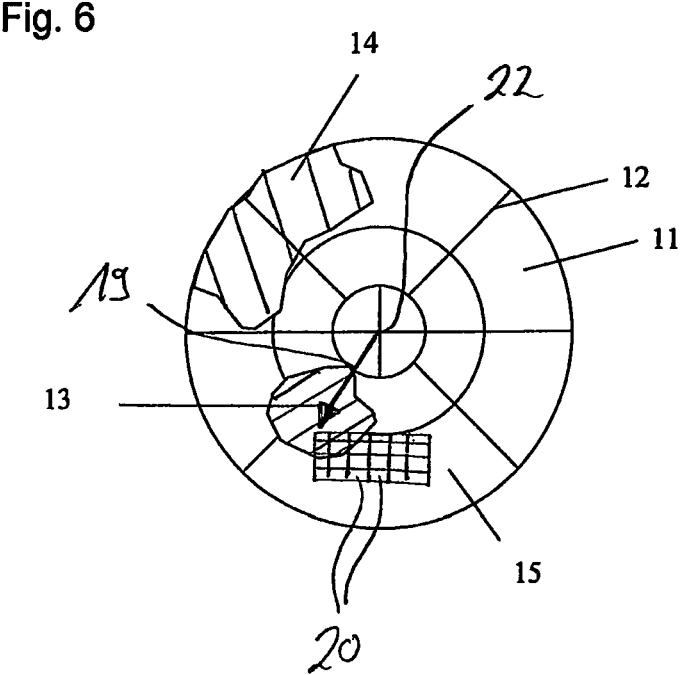
FIG. 6 shows a two-dimensional representation of the object of FIG. 3/FIG. 5.

When transforming the three-dimensional representation of the volume 16 as shown in FIG. 5 into a two-dimensional map as shown in FIG. 6 a two-dimensional transformation method is used. Preferably, the center axis 22 of the three-dimensional volume is used as the center of the two-dimensional map which spreads the surface of the three-dimensional volume as schematically shown by segments 11 and segment borders 12.

FIG. 6 thereby shows these segments 11 of the three-dimensional volume of FIG. 3 or FIG. 5 with a first subset of unit surfaces 20 (only partially displayed in FIG. 6) indicating a first level 13, second subset of unit surfaces 20 indicating a third level 14 and the rest of the unit surfaces 20 indicating a third subset, namely a second level 15, e.g. in grey colors. The representation of the volume in FIG. 6 displays a discrete acquisition time t1, . . . t6 with a certain area/region of the object being at a third level 14 and another area or region being at a first level 13 (e.g. blue colored) thereby indicating that the first area has a state in a first level 13 while the second area has another state in a third level 14 (e.g. red colored).

FIG. 6 also shows the propagation vector 19 which originates from the center axis 22 and points into the direction of the propagation of the contraction. Since the first area is in its first level 13, the propagation vector 19 leads into the direction of the contraction source of that area.

FIG. 7 shows six different acquisition times t1 . . . t6 wherein the three-dimensional volume 16 in accordance with FIG. 3 is shown above the two-dimensional representation of the surface of the three-dimensional volume 16. The first levels 13, second levels 15 and third levels 14 are visualized throughout two-dimensional areas on the two-dimensional map as well as on the three-dimensional surface 16, accordingly.

FIG. 7 shows the circular two-dimensional contraction front mapping of the left ventricle of a human's heart chamber thereby showing areas being at a first level 13 (contracted) and areas being at a third level 14 (expanded). By selecting times t1 . . . t6 the dynamic range of colors is aliased at both upper and lower limits. As a result the two-dimensional display shows only two colors, namely blue and red distinguished by the second level grey or white. By progressively advancing the time window through the cardiac cycle one can observe the areas that achieve peak contraction $t_p$ in a progressive fashion. This can then be displayed as a digital movie showing the mechanical peak contraction as a continuous wave throughout the left ventricle of the heart. The color coding of each static position of the surface of the heart enables the color mapping of all unit surfaces 20 and a continuous mapping of the propagation of the contraction wave of the heart. The resolution within a single frame can thereby be tuned to be as fine as necessary to resolve local differences by increasing the number of acquisition times and thus the number of frames as well as by increasing the number of volume units.

The example of FIG. 7 shows such a sequence of 6 static frames. The invention, however, enables to display these frames as part of a dynamic clip thereby being viewed as a movie. The propagation of a certain color over time over the two-dimensional map shows the temporal evolution of the contraction pattern and thus allows for an easy assessment of synchrony- or asynchrony and its propagation of the heart cycle. Such display can easily be compared with the mapping of electrophysiological potentials over time thereby comparing the excitation and contraction of the heart muscle.

As shown in FIG. 6 the propagation vector 19 can also be used in such movie representation. It is possible to create such propagation vector taking into account the spatial pattern of contraction in addition to temporal assessment. The two-dimensional vector represents both the quantity of myocardium in the left ventricle that has reached peak contraction and the mean direction of the contraction wave. This can be implemented as a moving arrow superimposed on the contraction front propagation. The origin of the vector is based preferably in the center 22 of the parametric image.

Additional vectors can be added for secondary sources of contraction designed in the same manner. This is e.g. necessary as some patients may display two or more waves of contraction as is seen after heart failure with significant dyssynchrony secondary to areas of scarring (electrical signals will delay as they circumvent scar and may result in two separate areas starting contract almost simultaneously) or in biventricular pacing.

An alternative vector representation of the propagation vector 19 can also be implemented by defining a vector with its origin in the area of earliest peak contraction, that is the area which reaches the first level 13 first, and the length and direction of the vector following the wave of peak contraction throughout the left ventricle. In the case of multiple wave spreading in various directions from the area of origin multiple propagation vectors 19 can be displayed in the same manner (multiple contraction vector mapping-MCVM).

The above described method can also be used for images which are acquired with CT or MR technology as long as the data is able to be transformed into a three-dimensional data set by using surface reconstruction and/or volume rendering techniques, and being able to be displayed as a three-dimensional data set over time.

What is claimed is:

1. Method for visualizing moments of an object, comprising:
    scanning an object by an image scanning apparatus to acquire at least two-dimensional cross-sectional images of said object at discrete acquisition times;
    digitalizing each of said cross-sectional images;
    recording each of said cross-sectional images and its corresponding position and acquisition time;
    transforming said cross-sectional images into a three-dimensional dataset;
    displaying said three-dimensional data set over time;
    partitioning the three-dimensional data set into a plurality of volume units, wherein each volume unit has a unit surface;
    calculating a change of volume of each volume unit over said acquisition times to obtain level information of each corresponding unit surface over time, wherein said level information corresponds to a time stamp derived from the function of the change of volume of each volume unit over time; and
    displaying said level information.

2. Method as claimed in claim 1, wherein said level information is allocated to a range of colors or a range of grey values.

3. Method as claimed in claim 1, comprising
    partitioning said three-dimensional data set into a plurality of volume units by using a center of gravity within said object and linking all corners of said unit surfaces with said center of gravity by straight lines.

4. Method as claimed in claim 1, comprising
    partitioning said level information using discrete level borders and allocating a limited number of colors to said discrete level information.

5. Method as claimed in claim 1, comprising
    displaying said level information three-dimensionally over time.

6. Method as claimed in claim 1, comprising
    displaying said unit surfaces and their corresponding level information two-dimensionally on a map by using a three-dimensional transformation method.

7. Method as claimed in claim 6, comprising
    displaying a propagation of said level information over time on said map, by additionally displaying a two-dimensional propagation vector.

8. Method as claimed in claim 7, comprising
    displaying a length and a direction of said two-dimensional propagation vector in relation to a direction and amount of volume change of the volume units.

9. Method as claimed in claim 1, comprising
    selecting said discrete acquisition times for a cardiac object in motion in accordance with an algorithm considering heart cycle variations by electrocardiographic gating and respiratory cycle variations by impedance measurements.

10. Apparatus for visualizing movements of an object, comprising
    ultrasonic scanning apparatus for scanning an object to acquire at least two-dimensional cross-sectional images of said object at discrete acquisition times;
    means for digitalizing each of said cross-sectional images;
    means for recording each of said cross-sectional images and its corresponding position and acquisition time;
    means for transforming said cross-sectional images into a three-dimensional data set;
    means for displaying said three-dimensional data set over time, means for partitioning the three-dimensional data set into a plurality of volume units, wherein each volume unit has a unit surface; and means for calculating a change of volume of each volume unit over said acquisition times to obtain level information of each corresponding unit surface over time, wherein said level information corresponds to a time stamp derived from the function of the change of volume of each volume unit over time, and wherein said displaying means display said level information.

11. Apparatus as claimed in claim 10, wherein said partitioning means partition said level information using discrete level borders and allocates a limited number of colors to said discrete level information, wherein said transforming means transform said unit surfaces with their respective level information two-dimensionally over time on a map by using a two-dimensional transformation method; and wherein said displaying means display said level information two-dimensionally.

12. Apparatus as claimed in claim 10, wherein said display means display a two-dimensional propagation vector, thereby displaying a length and a direction of said two-dimensional propagation vector in relation to a direction and amount of volume change of the respective volume units.

13. Apparatus as claimed in claim 10, further comprising electrocardiographic gating means and respiration trigger means for dynamically scanning cardiac objects.

14. Method as claimed in claim 7, wherein the moving object is the heart, and the two-dimensional propagation vector represents both a quantity of myocardium that has reached peak contraction and the mean direction of a contraction wave.

15. Method as claimed in claim 1, wherein the moving object is the heart, and the time stamp is the time necessary for each volume unit to reach its lowest volume.

16. Method as claimed in claim 1, comprising displaying said level information over time, wherein each time stamp will be allocated different colors when moving along time.

17. Method as claimed in claim 4, comprising displaying said level information dynamically, on a two-dimensional surface in a three-dimensional space, wherein the level borders are shifted over time, so that different colors are allocated to different time stamps over time.

* * * * *